United States Patent
Dinsmoor et al.

(10) Patent No.: US 9,439,581 B2
(45) Date of Patent: Sep. 13, 2016

(54) GUIDED MEDICAL ELEMENT IMPLANTATION

(75) Inventors: David A. Dinsmoor, St. Paul, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 2277 days.

(21) Appl. No.: 11/835,290

(22) Filed: Aug. 7, 2007

(65) Prior Publication Data

US 2008/0039738 A1 Feb. 14, 2008

Related U.S. Application Data

(60) Provisional application No. 60/932,961, filed on Aug. 11, 2006.

(51) Int. Cl.
| | |
|---|---|
| *A61B 5/053* | (2006.01) |
| *A61B 5/00* | (2006.01) |
| *A61B 17/00* | (2006.01) |
| *A61B 17/34* | (2006.01) |
| *A61N 1/05* | (2006.01) |
| *A61N 1/36* | (2006.01) |

(52) U.S. Cl.
CPC ............ *A61B 5/0536* (2013.01); *A61B 5/4504* (2013.01); *A61B 2017/00026* (2013.01); *A61B 2017/3407* (2013.01); *A61N 1/0551* (2013.01); *A61N 1/36007* (2013.01)

(58) Field of Classification Search
CPC .............. A61B 5/0536; A61B 5/4504; A61B 2017/00026; A61B 2017/3407
USPC .................... 600/407, 424, 425, 426
See application file for complete search history.

(56) References Cited

U.S. PATENT DOCUMENTS

| | | |
|---|---|---|
| 2,245,350 A | 6/1941 | Marshall |
| 3,001,070 A | 9/1961 | Davis, Jr. et al. |
| 4,541,432 A | 9/1985 | Molina-Negro et al. |
| 4,915,112 A | 4/1990 | Singer |
| 5,216,700 A | 6/1993 | Cherian |
| 5,242,455 A | 9/1993 | Skeens et al. |
| 5,284,153 A | 2/1994 | Raymond et al. |
| 5,311,878 A | 5/1994 | Brown et al. |
| 5,531,737 A | 7/1996 | Schade |
| 5,560,372 A | 10/1996 | Cory |

(Continued)

FOREIGN PATENT DOCUMENTS

| | | |
|---|---|---|
| EP | 1 239 768 B1 | 9/2002 |
| WO | WO 01/43630 | 6/2001 |

(Continued)

OTHER PUBLICATIONS

U.S. Appl. No. 11/835,296 to Stetz et al., entitled "Locating Guide," filed Aug. 7, 2007.

*Primary Examiner* — Peter Luong
(74) *Attorney, Agent, or Firm* — Shumaker & Sieffert, P.A.

(57) ABSTRACT

A system for locating a target tissue site is described. The system includes a locating guide that frames an area of interest upon placement over skin of a patient, an electrode patch defining an aperture and including two or more electrodes for placement within the area of interest, and a medical imaging device that indicates a location of a target tissue site within the patient based on electrical signals generated by one or more of the electrodes. A clinician may guide an introducer needle into the aperture for implanting a medical lead proximate to the target tissue site.

35 Claims, 9 Drawing Sheets

(56) References Cited

U.S. PATENT DOCUMENTS

| | | | |
|---|---|---|---|
| 5,775,331 A | 7/1998 | Raymond et al. | |
| 5,810,742 A | 9/1998 | Pearlman | |
| 6,055,452 A | 4/2000 | Pearlman | |
| 6,360,750 B1 * | 3/2002 | Gerber et al. | 128/898 |
| 6,405,732 B1 | 6/2002 | Edwards et al. | |
| 6,512,958 B1 | 1/2003 | Swoyer et al. | |
| 6,564,079 B1 | 5/2003 | Cory et al. | |
| 6,760,616 B2 | 7/2004 | Hoey et al. | |
| 6,847,849 B2 | 1/2005 | Mamo et al. | |
| 6,974,456 B2 | 12/2005 | Edwards et al. | |
| 7,050,848 B2 | 5/2006 | Hoey et al. | |
| 7,204,826 B2 | 4/2007 | Tremaglio et al. | |
| 2002/0072686 A1 | 6/2002 | Hoey et al. | |
| 2002/0147485 A1 | 10/2002 | Mamo et al. | |
| 2003/0216662 A1 * | 11/2003 | Jersey-Willuhn et al. | 600/547 |
| 2004/0015176 A1 | 1/2004 | Cosman | |
| 2004/0102721 A1 | 5/2004 | McKinley | |
| 2004/0103903 A1 | 6/2004 | Falahee | |
| 2004/0181165 A1 | 9/2004 | Hoey et al. | |
| 2005/0045191 A1 | 3/2005 | McKinley | |
| 2005/0109855 A1 | 5/2005 | McCombs | |
| 2005/0240238 A1 | 10/2005 | Mamo et al. | |
| 2006/0004422 A1 | 1/2006 | DeRidder | |
| 2006/0085048 A1 | 4/2006 | Cory et al. | |
| 2006/0085049 A1 | 4/2006 | Cory et al. | |
| 2008/0039866 A1 | 2/2008 | Stetz et al. | |

FOREIGN PATENT DOCUMENTS

| | | |
|---|---|---|
| WO | WO 01/87154 | 11/2001 |
| WO | WO 02/09584 | 2/2002 |
| WO | WO 2004/047874 | 6/2004 |
| WO | WO 2005/087314 | 9/2005 |

* cited by examiner

GUIDED MEDICAL ELEMENT IMPLANTATION

This application claims the benefit of U.S. Provisional Application No. 60/932,961, entitled "GUIDED MEDICAL LEAD IMPLANTATION," and filed on Aug. 11, 2006, the entire content of which is incorporated herein by reference.

TECHNICAL FIELD

The invention relates to implantable medical devices and, more particularly, implantation of medical leads.

BACKGROUND

Medical systems for tissue therapy often require the implantation of one or more medical elements proximate to a target tissue site. The medical element may be, for example, a medical lead to deliver electrical stimulation energy to the tissue or a catheter to deliver a fluid to the tissue. For some tissue therapy applications, a stimulation lead is implanted near a sacral nerve, which is a nerve bundle within the sacrum, a large triangular bone situated at the lower part of the vertebral column and at the upper and back part of the human pelvic cavity. There are multiple sacral nerves that pass through anterior and posterior sacral foramina of the sacrum.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Electrical stimulation is typically delivered to at least one of the S2, S3, or S4 sacral nerves using an electrical stimulator, which is coupled to the stimulation lead that is implanted proximate the sacral nerve.

In some cases, a medical element of a medical system is implanted through a sacral foramen (a single foramina) of a patient. For example, if selective stimulation of the S3 sacral nerve is desired, a medical lead may be introduced into the sacral foramen corresponding to the S3 sacral segment, which is commonly referred to as the "S3 sacral foramen." In one technique, a hollow introducer needle is advanced through the S3 foramen and the lead is advanced through a lumen of the hollow introducer needle until one or more electrodes near a distal end of the lead are positioned near the S3 sacral nerve. Stimulation energy is applied through the lead to the electrode to test the S3 nerve response. If necessary, the one or more electrodes are moved back and forth to locate the most efficacious location.

In some stimulation applications, a clinician generates a real-time image of the tissue of a patient using radiology in order to locate the target nerve site prior to implanting the medical lead. For example, a fluoroscope may be used to generate a real-time image of the internal structure of a patient in order to locate the target sacral foramen. Fluoroscopy generally requires a large apparatus, which requires a large space to house the apparatus, as well as specialized training to operate the fluoroscope.

SUMMARY

In general, the invention is directed toward systems and methods for locating a target tissue site within a patient, such as to implant a medical element (e.g., a medical lead, catheter or microstimulator or microsensor) proximate to the target tissue site. In some embodiments, the target tissue site includes a target nerve site, which may be a target nerve or a location of an anatomical structure providing access to the nerve. In some embodiments, a target tissue site locating system includes a locating guide, an electrode patch, and a medical imaging device that indicates a location of the target tissue site based on electrical signals generated by one or more electrodes. In one embodiment, the medical imaging device generates an image of the tissue composition of the patient near a target tissue site and presents the image on a display.

The locating guide may be placed over skin of the patient in the general vicinity of the target nerve site in order to define an area of interest. In some embodiments, the electrode patch is placed over skin within the area of interest and is movable within the area of interest relative to the locating guide. In other embodiments, the electrode patch and locating guide are mechanically coupled together and/or the relative positions between the electrode patch and locating guide are predefined. The imaging device may generate an image that indicates the composition of tissue of the patient underlying the electrode patch. A clinician may reference the image, locating guide, and electrode patch to register the image of the tissue composition to an actual location within patient, such as to implant a medical element proximate to the target tissue site. Locating a target tissue site may be useful for many medical therapy applications, such as for implanting a stimulation lead proximate to the target nerve site or implanting a catheter proximate to the target nerve site for drug delivery to the target nerve site.

In one embodiment, the invention is directed to a system comprising a locating guide that defines an area of interest upon placement over skin of a patient, an electrode patch defining an aperture and including two or more electrodes for placement within the area of interest, and a medical imaging device that indicates a location of a target tissue site within the patient based on electrical signals generated by one or more of the electrodes.

In another embodiment, the invention is directed to an assembly for locating a target tissue site in a patient. The assembly comprises a locating guide that defines an area of interest upon placement over skin of a patient, where the area of interest is in a general vicinity of the target tissue site. The assembly also comprises an electrode patch defining an aperture and including two or more electrodes for placement within the area of interest. A position of the electrode patch is adjustable with respect to the locating guide after the locating guide is placed over skin of the patient. The assembly further comprises a medical imaging device that indicates a location of the target tissue site within the patient based on electrical signals generated by one or more of the electrodes.

In another embodiment, the invention is directed to a method. The method includes positioning a locating guide over a portion of a patient to frame an area of interest, positioning an electrode patch within the area of interest. The electrode patch is movable within the area of interest and includes at least two electrodes. The method further comprises indicating a location of a tissue site within the patient based on electrical signals generated by one or more of the electrodes.

In another embodiment, the invention is directed to a system for locating a sacral foramen of a patient. The system comprises a locating guide for placing on skin of the patient, where the locating guide frames a region of skin proximate to a sacrum of the patient, an electrode patch defining an aperture and including two or more electrodes for placement within the region of skin proximate to the sacrum, and a medical imaging device that indicates a location of the sacral foramen based on electrical signals generated by one or more of the electrodes.

In another embodiment, the invention is directed to a method for locating a sacral foramen of a patient. The method comprises positioning a locating guide over at least a part of at least one of an Ilium bone or a spinal canal of the patient to frame a region of skin overlaying at least a part of a sacrum of the patient, positioning an electrode patch defining an aperture and including two or more electrodes for placement within the region of skin overlaying the sacrum, and locating the sacral foramen based on electrical signals generated by one or more of the electrodes.

The details of one or more embodiments of the invention are set forth in the accompanying drawings and the description below. Other features and advantages of the invention will be apparent from the description and drawings, and from the claims.

DETAILED DESCRIPTION

The invention relates to a noninvasive method and system for locating a target tissue site within a patient. The target tissue site may refer to the location of a target nerve or a location of an anatomical structure providing access to the nerve. As one example, the target tissue site may be a sacral nerve or a sacral foramen, through which a sacral nerve is accessible. In various embodiments described in this disclosure, a target tissue site is located using electrical impedance tomography (EIT) technology in combination with a locating guide and an electrode patch. The locating guide and electrode patch provide a clinician with EIT information concerning the location of a target nerve site within the patient to permit accurate implantation of the lead. However, similar non-radiological medical imaging technology may also be used. Advantageously, the use of a locating guide and electrode patch in combination with EIT may eliminate the need to use fluoroscopy for lead implantation. Alternatively, in some cases, EIT may be used in combination with fluoroscopy.

In some embodiments, determining the location of a target nerve site may be useful for implanting a medical member, such as, but not limited to, a medical lead, electrical stimulator or catheter, proximate to the target nerve site. Various embodiments of the invention may be applicable to different therapeutic applications requiring lead implantation, such as neuromodulation by electrical stimulation of or drug delivery to one or more sacral nerves, pudendal nerves (including perineal and/or dorsal nerve branch), genitofemoral nerves (including genital and/or femoral nerve branch), ilioinguinal nerves, and iliohypogastric nerves. Such neuromodulation techniques may be provided to alleviate a variety of symptoms or disorders, including pelvic pain, urinary incontinence, fecal incontinence, and sexual dysfunction. Other therapeutic applications may include electrical stimulation or drug delivery to one or more occipital nerves, e.g., for alleviation of headaches, cranial pain, or facial pain. The invention may be applicable to a variety of other therapeutic applications and tissue sites, including a variety of nerve sites, such as peripheral nerve sites. For purposes of illustration, however, the disclosure will refer to electrical stimulation of one or more sacral nerves, and will refer to a "target nerve site," although the locating guides described herein may also be useful for locating other target tissue sites.

Figure 1:
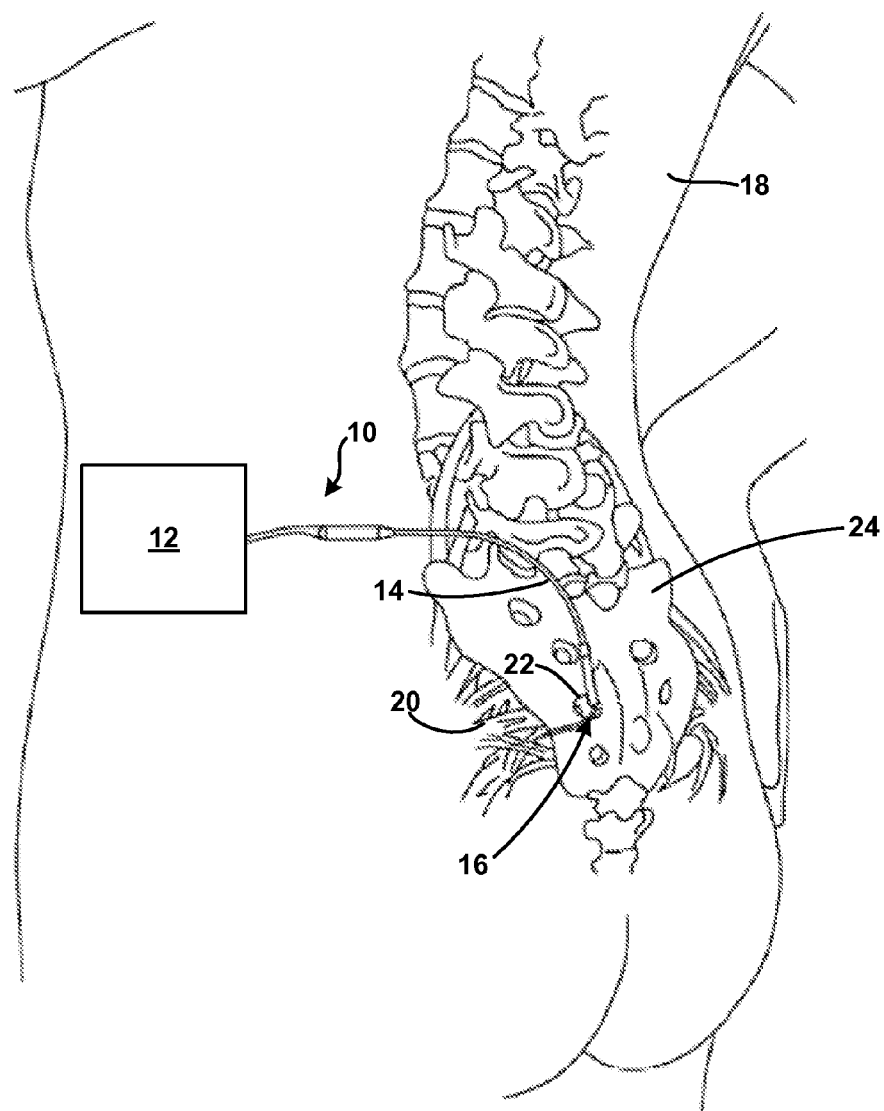
FIG. 1 is a schematic perspective view of a therapy system, which includes a medical device coupled to an implanted member that has been implanted proximate to a target nerve site located in accordance with the invention.

FIG. 1 is a schematic perspective view of therapy system 10, which includes medical device 12 coupled to implanted member 14. Implanted member 14 has been implanted proximate to target nerve site 16 in accordance with the invention. In particular, target nerve site 16 has been located in accordance with a system of the invention. In the embodiment of therapy system 10 shown in FIG. 1, target nerve site 16 is sacral foramen 20 of sacrum 24. Sacral foramen 22 provides access to sacral nerve 20. However, in alternate embodiments, target nerve site 16 may be any suitable nerve site in body 18, whether it is a nerve or an anatomical structure providing access to the nerve, and may be selected based on, for example, a therapy program selected for a particular patient. Similarly, the type of medical device 12 and implanted member 14 incorporated into therapy system 10 may also depend upon the selected therapy program.

For example, in the embodiment shown in FIG. 1, medical device 12 is an electrical stimulator (either implantable or external), which is directly or indirectly (e.g., via an extension) coupled to implanted member 14, which is a medical stimulation lead 14. Medical device 12 provides a programmable stimulation signal (e.g., in the form of electrical pulses or a continuous signal) that is delivered to target nerve site 16 by stimulation lead 14, and more particularly, via one or more stimulation electrodes carried by lead 14. In some cases, an electrical stimulator may also be referred to as a signal generator or a neurostimulator. In another embodiment, lead 14 may include one or more sense electrodes to permit medical device 12 to sense electrical signals from target nerve site 16, such as to sense one or more physiological parameters of patient 18 (e.g., blood pressure, temperature or electrical activity). Furthermore, in some embodiments, medical 12 may be coupled to two or more leads, e.g., for bilateral or multi-lateral stimulation and/or sensing.

While implanted member 14 is primarily referred to as a "medical lead" for the remainder of the description, in other embodiments, implanted member 14 may be any suitable medical element. For example, in another embodiments, medical device 12 may be a fluid delivery device, such as a drug pump, and medical element 14 may be a catheter that is placed to deliver a fluid (e.g., pharmaceutical agents, insulin, pain relieving agents, gene therapy agents or the like), from medical device 12 to target nerve site 16. In yet other embodiments, medical element 14 may be a substantially self-contained device that is not coupled to medical device 12, and therapy system 10 may not include medical device 12. For example, in some embodiments, implanted member 14 may be a leadless microstimulator, which includes a substantially self-contained device that includes stimulation and/or sensing electrodes and the associated electronics (e.g., controls, power source, and etc.) or a microstimulator with a lead that includes at least one stimulation and/or sensing electrode.

Figure 2:
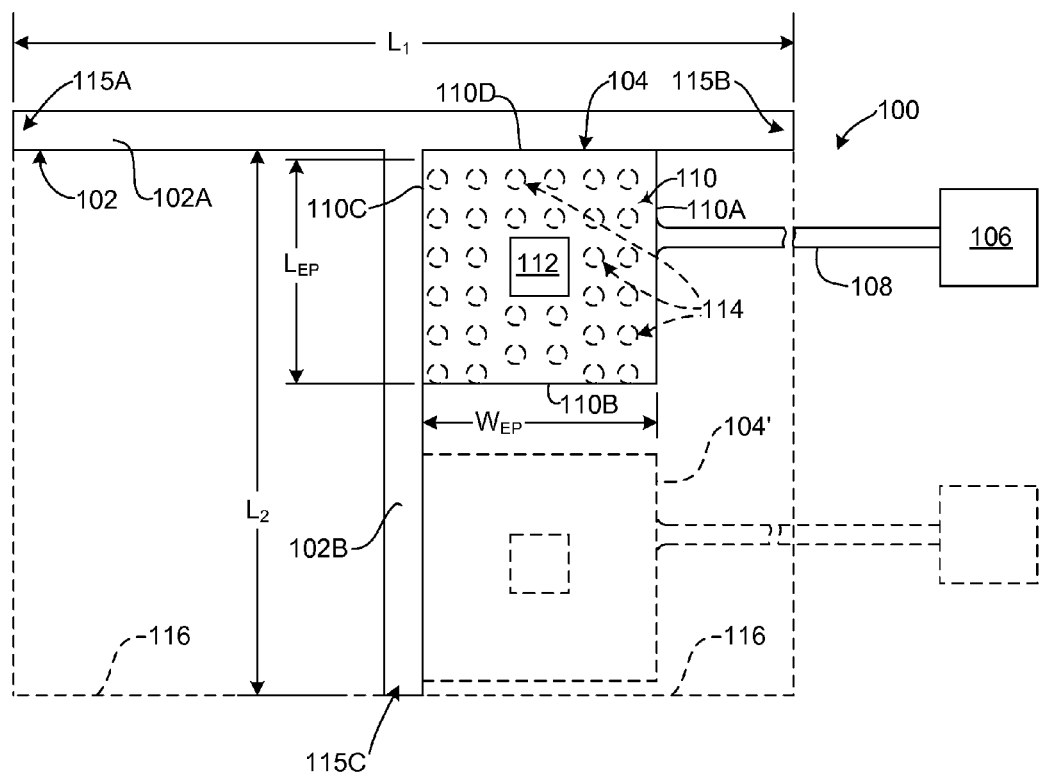
FIG. 2 is a plan view of a system for locating a target nerve site for implantation of a medical lead using an electrode patch and electrode impedance tomography (EIT), in accordance with an embodiment of the invention.

FIG. 2 is a plan view of system 100 for locating a target nerve site in accordance with an embodiment of the invention. System 100 may be particularly useful for locating a sacral nerve and a sacral foramen in a human patient. System 100 includes locating guide 102 and electrode patch 104, which is electrically coupled to EIT instrument 106 by one or more electrical conductors, such as a ribbon connector 108. In the example of FIG. 2, electrode patch 104 is a flexible circuit including nonconductive backing 110 defining aperture 112, and a plurality of skin surface electrodes 114 (shown in phantom in FIG. 2).

In general, locating guide 102 is placed on a patient's skin surface, and electrode patch 104 is subsequently positioned on the patient's skin adjacent to locating guide 102. EIT instrument 106 images the tissue underlying electrode patch 104. A clinician uses the resulting image to locate a target nerve site, e.g., the nerve to be stimulated or otherwise treated. After locating the target nerve site, the clinician may guide an introducer needle (not shown) into the patient near the target nerve site and guide a medical lead, catheter, or other implantable device through the introducer needle for implantation proximate to the target nerve site. In the case of a medical lead, for example, the introducer needle may be used to implant a distal electrode carried by the lead proximate to the target nerve site. Although the techniques described in this disclosure may be useful for implantation of leads, catheters, leadless stimulators and other devices, implantation of leads will be generally described for purposes of illustration. A catheter may be placed to deliver a fluid, such as pharmaceutical agents, insulin, pain relieving agents, gene therapy agents, or the like from a fluid reservoir and/or pump. A leadless stimulator may refer to a self-contained microstimulator including power generation circuitry, stimulation circuitry, and electrodes in an integrated housing sized for introduction via a needle or other minimally invasive introducer.

In some embodiments, both locating guide 102 and electrode patch 104 are disposable after use with a single patient. In other embodiments, locating guide 102 and/or electrode patch 104 may also be reusable. Of course, if either locating guide 102 or electrode patch 104 is reused for multiple patients, locating guide 102 and/or electrode patch 104 should be appropriately sterilized.

Locating guide 102 is configured to provide an initial reference point for a clinician to position electrode patch 104 in the general vicinity of the target nerve site. Locating guide 102 may be formed of any suitable flexible material, such as, but not limited to, polyimide (e.g., Kapton brand polyimide film, which is available from E. I. du Pont de Nemours and Company of Wilmington, Del.) or silicon. In another embodiment, locating guide 102 may be formed of a substantially rigid material that is contoured to fit over a backside of a patient, or another surface of the patient near a target nerve site. While a contour of a backside may differ substantially between patients, a contour of locating guide 102 may be based on an average contour of a backside of, for example, adult humans. In yet another embodiment, locating guide 102 may be formed of a material that is pliable enough to adapt to different skin surface contours, while at the same time, hold its shape. Locating guide 102 is preferably formed of a material having a color that allows locating guide 102 to be easily distinguished from skin on which it is placed.

An adhesive may be placed along a surface of locating guide 102 in order to attach locating guide 102 to a patient's skin at a desired position. Examples of suitable adhesives include adhesives used for ground electrode pads and electrocardiogram (ECG) electrode pads, which may be, for example, tragacanth gum, karaya gum, or acrylates. In other embodiments, other modes of attachment that enable locating guide 102 to be placed on skin of a patient and substantially remain in place may be used. For example, locating guide 102 may include a belt that extends around a waist of a patient or connects to a surface on which patient 18 is placed (e.g., a table or bed), or alternatively, locating guide 102 may include Velcro attachments in regions 115A, 115B, and/or 115C that mate with strips already attached to the patient. In yet another alternative embodiment, locating guide 102 may be formed of a material that exhibits a high coefficient of friction with human skin, which enables locating guide 102 to remain substantially in place when placed on skin.

Preferably, a size of locating guide 102 remains the same for all patients. Of course, if desired, a clinician may be given the option to choose from a variety of locating guides 102 having different sizes for different patients. In the embodiment shown in FIG. 2, dimension $L_1$ of locating guide 102 is approximately 13 centimeters (cm) to about 15 cm and dimension $L_2$ is approximately 13 cm to about 15 cm. The $L_1$ and $L_2$ values are merely exemplary, and locating guide 102 may be any suitable size.

Figure 5:
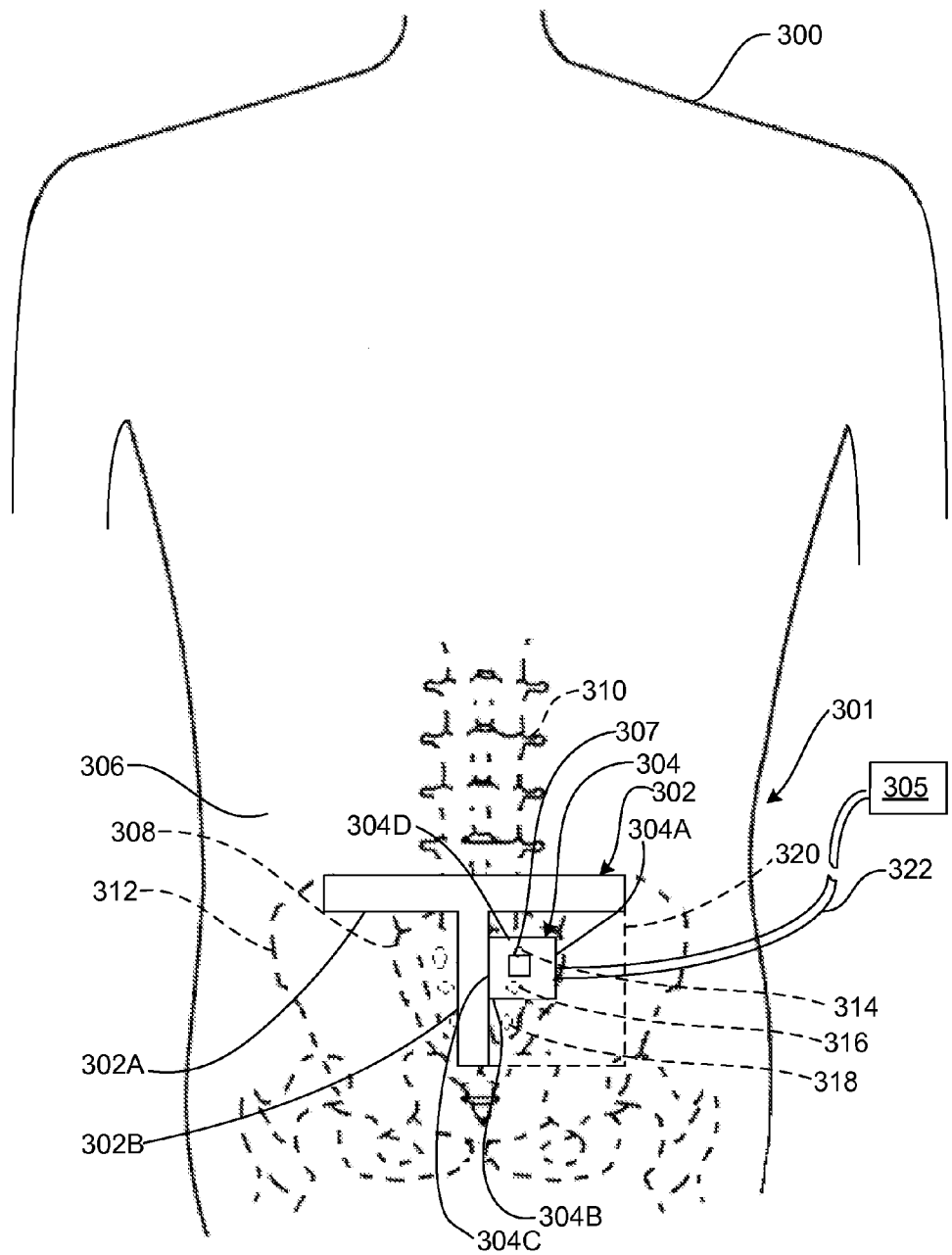
FIG. 5 is a backside view of a patient and illustrates an electrode patch and locating guide placed over the patient's skin near the sacrum in accordance with an embodiment of the invention.

In the embodiment shown in FIG. 2, a shape of locating guide 102 may be dictated by the boney landmarks on the patient's back near the sacrum. In the example of FIG. 2, locating guide 102 is generally a T-shape, which allows first portion 102A to overlay the posterior protuberance (or "crest") of the patient's Ilium bone (i.e., where the sacroiliac ligament attaches to the Ilium) and second portion 102B to overlay a part of the patient's spinal canal, which runs through the center of the sacrum. In this way, locating guide 102 frames the general location of the sacrum and sacral foramen, examples of which are shown in FIG. 5. By framing the general location of the sacral foramen, locating guide 102 frames area of interest 116 (outlined by phantom lines) in which the clinician may place electrode patch 104.

In alternate embodiments, the size and shape of locating guide 102 are adjusted to accommodate other applications of system 100, which may affect the boney landmarks locating guide 102 overlays. The relevant boney landmarks depend upon the medical lead implantation site, which is typically dictated by the tissue stimulation application. For example, in other embodiments, locating guide 102 may have a shape that approximates a shape of sacrum 24.

In addition to providing a general starting point for a clinician to approximate the location of the sacral foramen, locating guide 102 provides a stationary reference point for the clinician if the clinician readjusts the position of electrode patch 104 within area of interest 116. In addition, locating guide 102 may provide a coordinate system to record different positions of electrode patch 104 during the course of EIT mapping. After placing electrode patch 104 over one portion of area of interest 116 framed by locating guide 102, the clinician may want to reposition electrode patch 104, as shown by the phantom electrode patch 104' in FIG. 2. For example, the clinician may discern from the resulting EIT image that electrode patch 104 is not positioned over a sacral foramen or that aperture 112 in nonconductive backing 110 of electrode patch 104 is not as close as desired to the sacral foramen. Electrode patch 104 may be repositioned as many times as necessary to locate the target sacral foramen/target nerve site. Each new position of electrode patch 104 can be referenced to locating guide 102.

Locating guide 102 preferably remains in the same position on the patient throughout the medical lead implantation procedure. In this way, locating guide 102 provides a relatively stationary reference point for the clinician to visually track each position of electrode patch 104. For example, locating guide 102 provides a reference point for comparing the position of a repositioned electrode patch 104 with an initial position of electrode patch 104 without having to physically mark the patient's skin (e.g., with ink).

After EIT instrument 106 generates an image of the subcutaneous tissue underlying electrode patch 104, locating guide 102 helps relate the imaged tissue to actual locations within area of interest 116 framed by locating guide 102. This helps the clinician locate the foramen (or a peripheral nerve).

Both locating guide 102 and electrode patch 104 include a "skin contact side," which is defined by a surface of locating guide 102 and electrode patch 104, respectively, that is intended to contact a patient's skin. In FIG. 2, the skin contact side is facing into the image, and thus, is not shown. The skin contact side of locating guide 102 and electrode patch 104 are preferably chemically and biologically inert so as not to react with skin or other surfaces and materials (e.g., common sterilizing agents such as isopropyl alcohol) that may be contacted by locating guide 102 and electrode patch 104, respectively, during normal use of system 100.

The skin contact side of electrode patch 104 is the surface that includes electrodes 114, which preferably contact the patient's skin in order for electrodes 114 to deliver current to and receive electrical signals from the skin of the patient. Electrodes 114 are attached to a skin contact side of nonconductive backing 110 in any suitable arrangement, such as a random arrangement or a matrix comprising of a series of rows and columns, in which electrodes may be linearly aligned, e.g., like a grid, or staggered, e.g., like a checkerboard. The number and size of electrodes 114 may be adjusted for the particular application of system 100. For example, in an application in which a sacral nerve/foramen is located, electrode patch 104 may include a matrix of approximately one-hundred equally spaced electrodes 114 about one millimeters (mm) to about 3 mm in diameter, e.g., arranged in approximately ten rows and ten columns of electrodes, but omitting electrodes that would otherwise reside within aperture 112. The matrix may be square or rectangular, such that the number of electrodes 114 in a given row may be the same as or different from the number of electrodes in a given column. The spacing between electrodes 114 may be about 1 mm to about 10 mm between outer edges of adjacent electrodes 114. Other arrangements of electrodes 114 are also contemplated, and are not limited to any particular pattern or shape.

In FIG. 2, only thirty-two electrodes 114 are shown purely for illustration, and the depiction of thirty-two electrodes 114 is not intended to limit the scope of invention in any way. Rather, a lesser number of electrodes 114 are shown in FIG. 2 for ease of illustration. In general, the more electrodes 114 that are disposed on electrode patch 104, the higher the resolution of the resulting impedance image generated by EIT instrument 106 will be. The size of electrode patch 104 may also depend upon the particular application of system 100. For the sacral nerve locating application, width $W_{EP}$ of electrode patch 104 may be about 9 cm to about 15 cm and length $L_{EP}$ of electrode patch 104 may be about 5 cm to about 9 cm. In one embodiment, width $W_{EP}$ of electrode patch 104 may be about 7.62 cm (3.0 inches) and length $L_{EP}$ may be about 12.70 centimeters (5 inches). However, electrode patches 104 having other sizes are also useful.

In some embodiments, electrodes 114 may take the form of skin surface electrodes in the form of electrode pads or bumps, which may have a variety of shapes, e.g., square, rectangular, triangular or circular. In an alternate embodiment, one or more of the electrodes 114 may be a small gauge percutaneous needle, such as an acupuncture needle, rather than a skin surface electrode in order to probe deeper into the patient's skin, which may help generate a more accurate electrode impedance image. In general, the closer to the nerve tissue electrodes 114 in electrode patch 104 are positioned, the higher the resolution of an image outputted by EIT instrument 106 will be.

Nonconductive backing 110 is preferably flexible to enable electrode patch 104 to conform to different body surfaces, and thus, a number of different applications. Nonconductive backing 110, as well as locating guide 102, may be composed of materials typically used in flexcircuits including, but not limited to, polyimide and silicon. Electrodes 114 may be printed, deposited, or otherwise formed on a surface of nonconductive backing.

Aperture 112 defined by nonconductive backing 110 of electrode patch 104 is sized large enough to receive an introducer needle for an implantable medical lead 14 or another medical member (also referred to as a medical element). In addition, aperture 112 is preferably large enough to provide room to adjust the path of the introducer needle within aperture 112. For example, in one embodiment, aperture 112 is at least about 3 mm to about 15 mm by 3 mm to about 15 mm, and is preferably 5 mm by 5 mm. In alternate embodiments, aperture 112 is configured to receive other means of introducing a medical lead into a patient's tissue. Furthermore, although aperture 112 is illustrated in FIG. 2 as having a square shape and centered with respect to outer edges 110A, 110B, 110C, and 110D of nonconductive backing 110, in alternate embodiments, aperture 112 may be any suitable shape and/or not centrally located in nonconductive backing 110. For example, aperture 112 may be a circular shape having a diameter in a range of about 3 mm to about 15 mm. If desired, a clinician may also introduce the needle through portions of electrode patch 104 other than aperture 112 by poking the needle through nonconductive backing 110. However, with a predefined aperture 112 in nonconductive backing 110, the clinician is assured that the needle will not interfere with one of the electrodes 114 when the needle is introduced through aperture 112 to reach target tissue site 16 (FIG. 1).

A conductive adhesive may be used to attach electrode patch 104 to skin of a patient. As with locating guide 102, suitable adhesives include, but are not limited to, tragacanth gum, karaya gum, acrylates, and conductively loaded hydrogels. In some embodiments, a conductive additive may be added to the adhesive in order to promote the conductivity between each of the electrodes 114 and the skin of the patient. In an alternative embodiment, a conductive gel, such as a NaCl gel (comprised of NaCl and a gelling agent), may be used as the adhesive. It may be important for the conductive adhesive or gel to be isolated between the individual electrodes 114 of the electrode patch 104 in order to prevent shorts between pairs of electrodes 114. If such shorts occur, the performance of the EIT instrument may be adversely affected. The use of a gel also helps prevent DC offsets and electrode polarizations, which may lead to undesirable results.

In alternate embodiments, other suitable means of adhering electrode patch 104 to skin may be used. Preferably, the adhesion means on electrode patch 104 enable electrode patch 104 to be adhered and re-adhered to skin a multiple number of times to allow for the situation in which electrode patch 104 is repositioned. In addition, a nonconductive adhesive may be placed about the outer periphery of nonconductive backing 110 in order to further secure electrode patch 104 in place on the patient's skin.

Electrode patch 104 may be formed using any suitable method known in the art for forming a medical electrode patch, such as circuit technology or MEMs (microelectrical mechanical systems) technology. In embodiments utilizing circuit technology to form electrode patch 104, a flexible or rigid circuit board material may be used. For example, in one embodiment, a flexible copper-plated polyimide polymer sheet is etched (e.g., using a photoresist and ferric chloride solution) to define electrode pads and conductive traces that may be soldered to separate conductors of ribbon conductor 108. The copper traces are masked and nickel is electroplated onto the electrode pads. Gold is then electroplated onto the nickel electroplated electrode pads to complete electrodes 114. Another polyimide polymer layer is laminated over the traces to electrically insulate the traces, thereby completing electrode patch 104. In another embodiment, the copper traces may be printed onto the polyimide polymer sheet.

Ribbon conductor 108 electrically couples electrodes 114 of electrode patch 104 to EIT instrument 106. Each electrode 114 in electrode patch 104 is typically connected to a separate conductive path in ribbon conductor 108, where each conductive path is electrically insulated. However, in some embodiments, more than one electrode 114 may be coupled to a common conductive path. Any suitable conductor, such as, but not limited to, electrical traces and wires, may be substituted for ribbon conductor 108 in order to electrically couple electrodes 114 of electrode patch 104 with EIT instrument 106.

In an alternate embodiment, electrodes 114 of electrode patch 104 may be wirelessly connected to EIT instrument 106. In such an embodiment, electrode patch 104 includes a source of power (e.g., batteries), a stimulation engine, a sensing system, and a wireless telemetry system.

EIT instrument 106 may be a non-radiological medical imaging apparatus known in the art. Some conventional methods for implanting a sacral nerve stimulation lead 14 rely on fluoroscopy to identify the location of the relevant sacral foramen 22 for accessing the desired sacral nerve 20. One disadvantage of relying on fluoroscopy for a lead implantation procedure is that the fluoroscope is typically located in a hospital operating room suite, and as a result, the fluoroscopy procedure is typically an in-patient procedure. In addition, operation of the fluoroscope requires specialized training and access to a fluoroscope, which is relatively costly.

In contrast, system 100 of the invention utilizes EIT instrument 106 to generate an image of the tissue composition of a patient in the general vicinity of target nerve site 16 in order to locate target nerve site 16, or otherwise indicate a location of a nerve site. EIT instrument 106 provides a space and cost-effective alternative to fluoroscopy. EIT instrument 106 can be constructed smaller than a fluoroscope and other radiological machines, potentially enabling a clinician to implant lead 14 within patient 18 in an out-patient setting (e.g., in the clinician's office rather than in a hospital). In addition, the use of EIT instrument 106 typically requires less training than a fluoroscope.

Figure 3:
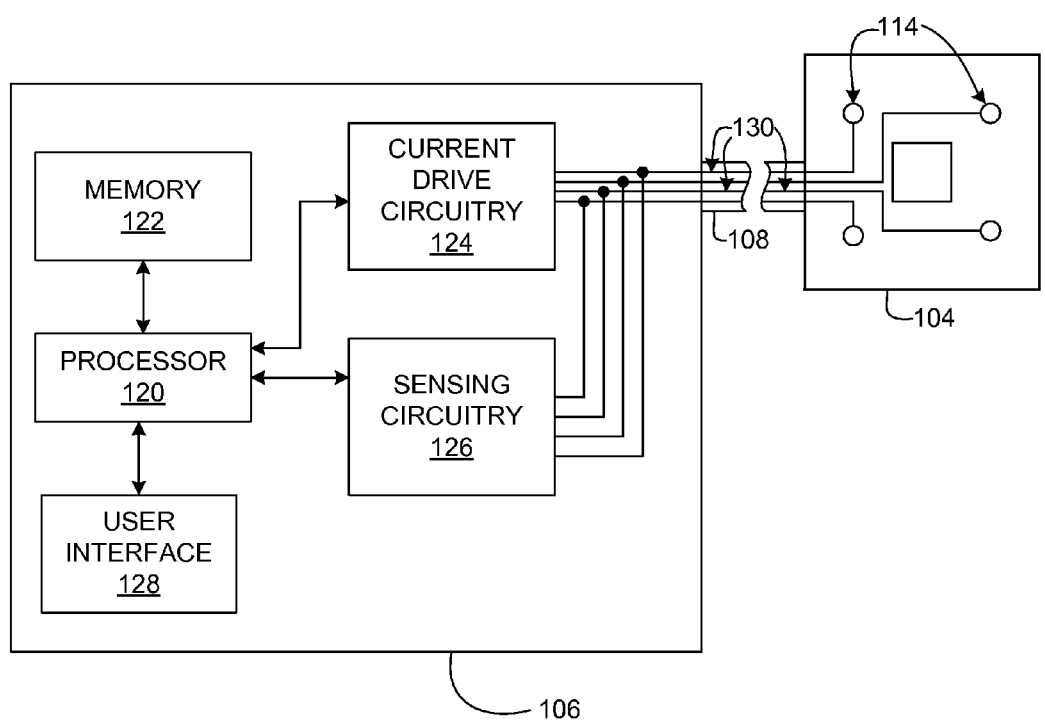
FIG. 3 is a functional block diagram illustrating EIT instrument.

EIT instrument 106 noninvasively determines the composition or configuration of tissue underlying electrode patch 104, permitting identification of the spatial location of target nerve site 16. As previously described, target nerve site 16 is not limited to the sacral foramen 22, but includes other target tissue sites within patient 18. FIG. 3 is a functional block diagram illustrating EIT instrument 106. In the illustrated example, EIT instrument 106 includes processor 120, memory 122, current drive circuitry 124, sensing circuitry 126, and user interface 128. In FIG. 3, electrode patch 104 is shown coupled to EIT instrument 106 via ribbon connector 108. Four electrodes 114 are shown in FIG. 3 for ease of illustration. However, as previously discussed, electrode patch 104 may include any suitable number of electrodes in any suitable arrangement. Electrodes 114 are shown electrically coupled to current drive circuitry 124 and sensing circuitry 126 by separate conductors 130 of ribbon connector 108

Processor 120 controls current drive circuitry 124 and sensing circuitry 126. Processor 120 may include any one or more of a microprocessor, a controller, a digital signal processor (DSP), an application specific integrated circuit (ASIC), a field-programmable gate array (FPGA), discrete logic circuitry, or the like. Memory 122 may store one or more programs that define which electrodes, i.e., electrical paths, are to be used to determine impedance. Memory 122 may include for example any volatile, non-volatile, magnetic, optical, or electrical media. For example, memory 122 may include any one or more of a random access memory (RAM), read-only memory (ROM), non-volatile RAM (NVRAM), electronically erasable programmable ROM (EEPROM), flash memory, or the like. Memory 122 may also store EIT data generated by EIT instrument 106, such as generated images. User interface 128 may include a display, and an input mechanism, such as a touch-screen display, keyboard, keypad, joystick, mouse, or other peripheral input devices. The clinician may interact with EIT instrument 106 via user interface 128, such as to initiate the generation of an EIT image.

Processor 120 may control current drive circuitry 124 to deliver a number of sub-threshold electrical currents between different pairs of electrodes 114 via conductive paths 130 in ribbon connector 108. A sub-threshold electrical current is a current that is substantially unnoticeable by a patient, and includes a pulse having an amplitude or pulse width significantly lower than that of therapeutic stimulation pulses (i.e., below a threshold sufficient to result in an action potential on the nerve). Because of their low amplitude and/or pulse width, such sub-threshold currents may not result in any therapeutic or adverse effects, e.g., may not be above a threshold sufficient to activate any nerves or other tissues.

Sensing circuitry 126 measures the electrical potentials sensed between electrodes 114 from the different electrode 114 pairings and applied currents. Sensing circuitry 126 may include amplifiers, filters, analog-to-digital converters, or other circuitry. Processor 120, which includes impedance measurement circuitry, combines, and analyzes the resulting electric potentials using any of a variety of known techniques. The impedance measurement circuitry may include resistors, capacitors, or other known circuitry for sampling and/or holding a value of current when a signal is delivered by current drive circuitry 124.

The EIT technique assumes that tissue resistivities and dielectric constants are stable in the presence of the applied electrical fields. Processor 120 typically uses a reconstruction algorithm to generate an impedance image that corresponds to the tissue structure underlying electrode patch 104. Reconstruction algorithms or the like used by processor 120 to determine the impedance may be stored in memory 122. The resulting image may be outputted via user interface 128. In short, different types of tissue exhibit different resistivity values, which enables EIT instrument 106 to generate an image that reflects the different types of tissue underlying electrodes 114. The image is typically a two-dimensional image presented on a display, such as an LCD monitor or a CRT monitor, and the presence of a nerve is typically represented as an area with the highest relative impedance because of the electrical characteristics of nerve tissue.

In other embodiments, EIT instrument 106 may use other modes of indicating a location of a target nerve site. In one alternative embodiment, EIT instrument 106 may "image" a tissue composition based on electrical signals generated by electrodes 114 of electrode patch 104, and indicate a target nerve site by generating an audible or visible indication (e.g., a light may turn on) when aperture 112 in electrode patch 104 is in a correct location near the target nerve site. For example, EIT instrument 106 may interpret impedance measurements of the tissue underlying electrode patch 104 as electrode patch 104 is moved around (e.g., within area of interest 116 defined by locating guide 102).

In another alternative embodiment, EIT instrument 106 may image the tissue composition underlying electrode patch 104 and provide directions for locating the target nerve site based on an impedance analysis. For example, processor 120 of EIT instrument 106 may include circuitry that determines whether a location exhibits an impedance at or above a certain value, which may indicate the presence of a nerve site. If the location exhibits an impedance at or above a certain value, EIT instrument 106 may provide an output to the clinician. The output may be in the form of an audible or visible indication, or directions with respect to a locating guide. For example, the EIT instrument may provide x-y coordinates indicating a location of a target nerve site.

EIT instrument 106 may be any conventional and/or commercially available EIT instrument, such as, but not limited to, a Nervonix Nerve Imaging instrument from Nervonix, Inc. of Bozeman, Mont. or an instrument as described in U.S. Patent Application No. 2006/0085049, entitled, "ACTIVE ELECTRODE, BIO-IMPEDANCE BASED, TISSUE DISCRIMINATION SYSTEM AND METHODS OF USE."

In alternate embodiments, other medical imaging devices that determine the composition or configuration of tissue underlying the surface of the skin based on the different electrical characteristics of tissue may be substituted for EIT instrument 106. As known in the art, many forms of subcutaneous tissue in the human body are responsive to electrical signals. Different types of tissue exhibit different responses to electrical signals based on the impedance, resistivity and dielectric constant of the tissue. For example, it has been found that nerve tissue includes a higher concentration of ion channels per gram of tissue relative to other tissue (e.g., muscle). As a result, these methods are useful for identifying the location of target nerve sites, including peripheral nerves.

Figure 4:
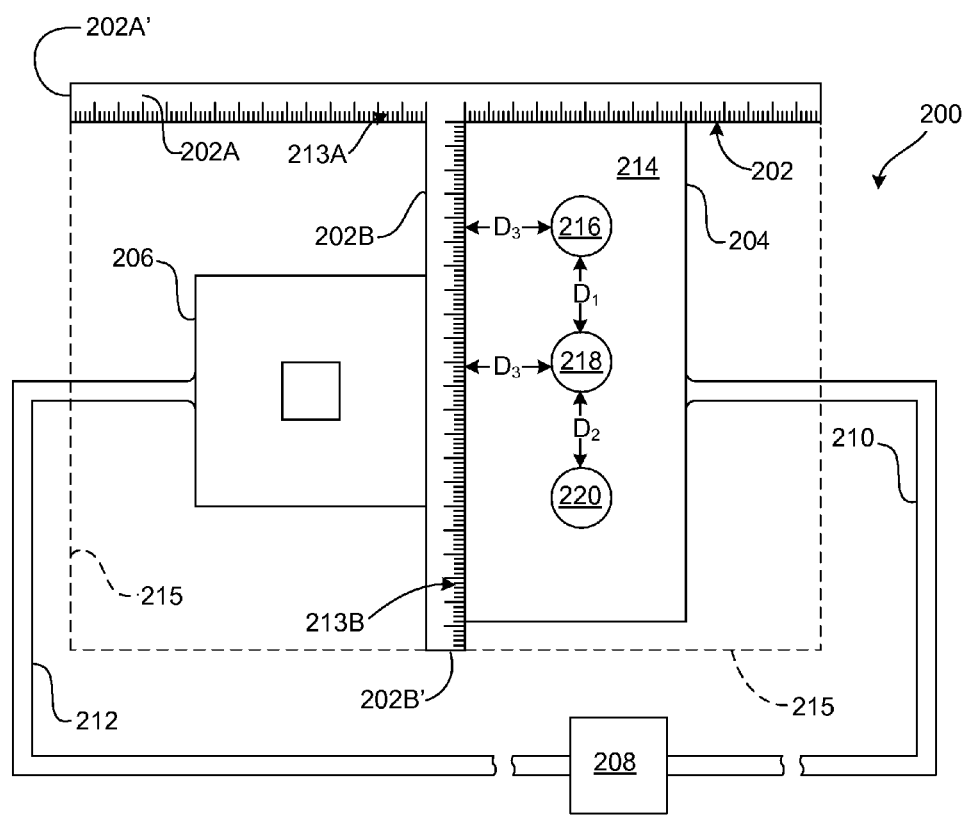
FIG. 4 is a plan view of a system for locating a target nerve site for implantation of a medical lead using multiple electrode patches and EIT, in accordance with another embodiment of the invention.

FIG. 4 is a plan view of nerve site locating system 200, which is an alternate embodiment of system 100 of FIG. 2. System 200 includes locating guide 202, first electrode patch 204, second electrode patch 206, and EIT instrument 208. First electrode patch 204 is electrically coupled to EIT instrument 208 by ribbon connector 210, and second electrode patch 206 is electrically coupled to EIT instrument 208 by ribbon connector 212.

Locating guide 202 is similar to locating guide 102 of system 100 of FIG. 2, except that locating guide 202 includes distance marks 213A and 213B (collectively distance marks 213). Distance marks 213 may aid a clinician during a repositioning of electrode patches 204 and 206 within area of interest 215 (in phantom) framed by locating guide 202. For example, the clinician may reposition locating guide 202 relatively accurately and precisely based on reference marks 213. In addition, distance marks 213 provide visual indicia for relating the imaged tissue to actual locations within area of interest 215. In one embodiment, distance marks 213 may be labeled with numbers representing units of measurement. Any suitable unit of measurement may be used, including, but not limited to, millimeters, centimeters, and inches. Alternatively, distance marks 213 may merely be numbered consecutively, rather than representing units of measurement. Other numbering schemes may also be used.

In one embodiment, distance marks 213A along first portion 202A represent x-axis coordinates, while distance marks 213B along second portion 202B represent y-axis coordinates. Together, distance marks 213 may be used to form an x-y coordinate system for identifying a specific location within area of interest 215 framed by locating guide 202. The x-axis coordinates may begin (i.e., a zero position), for example, at end 202A' of first portion 202A of locating guide, while the y-axis coordinates may begin at end 202B' of second portion 202B.

An x-y coordinate system, or another type of coordinate system, may be useful for identifying a specific location within area of interest 215. For example, EIT instrument 208 may generate an image including x-y coordinates that substantially match or otherwise correspond to the x-y coordinates provided by distance marks 213. A clinician may easily relate a location within the image to an actual location within area of interest by matching the x-y coordinates from the image to the x-y coordinates within area of interest 215. In another example, EIT instrument 208 may indicate a target nerve site by outputting x-y coordinates, rather than generating an image. EIT instrument 208 may also output or otherwise indicate a target nerve site by outputting a vector value representing a length and angle with respect to an x-y coordinate position. Furthermore, EIT instrument 208 may store x-y coordinates (or vector values) in memory for various target nerve sites for a particular patient for immediate and/or later use by the clinician.

As with locating guide 102, in the example of sacral stimulation, first portion 202A of locating guide 202 is configured to overlay the crest of the patient's Ilium bone and second portion 202B is configured to overlay a part of the patient's spinal canal.

Electrode patch 204 is similar to electrode patch 104 of system 100 of FIG. 2 except that nonconductive backing 214 of electrode patch 204 defines a plurality of apertures 216, 218, and 220, which are circular. In alternate embodiments, electrode patch 204 may include any suitable number of apertures having any suitable shape. A plurality of apertures 216, 218, and 220 provide more than one opening through which an introducer needle may be introduced into the tissue underlying electrode patch 204 to access target nerve site 16. Furthermore, electrode patch 204 covers a larger area of the area of interest framed by locating guide 202 compared to electrode patch 110 of FIG. 2. In combination with the additional apertures 216, 218, and 220, a clinician may not need to readjust the position of electrode patch 204 in order to locate the sacral foramen, as with system 100 of FIG. 2. The presence of more than one aperture 216, 218, and 220 helps increase the possibility that at least one aperture 216, 218 or 220 aligns with target nerve site 16.

Plurality of apertures 216, 218, and 220 in nonconductive backing 214 of electrode patch 204 also enables a clinician to locate more than one foramen at a time, and implant more than one medical lead in patient 18 without having to readjust the location of electrode patch 204. For example, apertures 216, 218, and 220 may each correspond to a sacral foramen (e.g., aperture 216 is configured to align with the S2 foramen, while aperture 218 is configured to align with the S3 foramen and aperture 220 is configured to align with the S4 foramen).

The distances between each sacral foramen may differ based on the patient, thus, distances $D_1$ between apertures 216 and 218, distance $D_2$ between apertures 218 and 220 may not accurately represent the distances between a particular patient's foramen. However, distances $D_1$ and $D_2$ may be generic enough to match a large range of patients. The average distance may consider the difference in distances between the S1 and S2 sacral foramina and the S2 and S3 foramina, and so forth. For example, if aperture 216 is configured to align with the S2 foramen, aperture 218 is configured to align with the S3 foramen, and aperture 220 is configured to align with the S4 foramen, distance $D_1$ may be calculated based on the average distance between an adult human's S2 and S3 sacral foramina, and distance $D_2$ may be calculated based on the average distance between an adult human's S3 and S4 sacral foramina. Based on one measurement, the average distance between an adult human's S4 and S3 sacral foramina is about 1.8 cm, while the average distance between an adult human's S3 and S2 sacral foramina is about 2.3 cm. If apertures 216, 218, and 220 are configured to align with other sacral foramen, distances $D_1$ and $D_2$ may differ. Based on one measurement, the average distance between an adult human's S1 and S2 sacral foramina is about 2.6 cm, while the average distance between an adult human's S4 and S5 sacral foramina is about 1.5 cm.

In another embodiment, distances $D_1$ and $D_2$ may be in a range from about 1.5 cm to about 2.6 cm, which represents an average distance between sacral foramina. In addition, distances $D_3$ between the center of the sacrum (which is represented by portion 202B of locating guide 202) and each foramen varies based on the specific anatomy of the patient. However, the average distance $D_3$ is about 1.5 cm to about 2.5 cm.

In an alternate embodiment, rather than utilizing one electrode patch 204 with multiple apertures 216, 218, and 220, more than one electrode patch (each including a single aperture or multiple apertures) may be substituted for electrode patch 204. The multiple electrode patches may be placed adjacent to one another.

In addition to electrode patch 204, system 200 includes a second electrode patch 206 positioned on an opposite side of locating guide 202 than first electrode patch 204. First and second electrode patches 204 and 206 are connected to the same EIT instrument 208. In an alternate embodiment, first and second electrode patches 204 and 206 may be electrically coupled to different EIT instruments.

More than one electrode patch 204 or 206 may be used in order to locate more than one sacral foramen at a time. For example, sacral foramina are located on either side of the spinal canal. As previously stated, portion 202B of locating guide 202 is configured to overlay a part of the patient's spinal canal. Thus, in order to locate sacral foramina on both sides of the spinal canal, it may be desirable to utilize electrode patches 204 and 206 on opposite sides of portion 202B of locating guide 202. Implantation of leads in foramina on opposite sides may be desirable for achieving simultaneous or alternating bi-lateral therapy delivery, e.g., stimulation.

FIG. 5 is a backside view of patient 300 and illustrates system 301 in accordance with the invention for locating a sacral nerve in order to implant a medical lead near the sacral nerve. System 301 may generally conform to system 100 of FIG. 2, system 200 of FIG. 2, or system 500 of FIG. 8 respectively, and may include locating guide 302, and at least one electrode patch 304 defining at least one aperture 307, and EIT instrument 305. Locating guide 302 and electrode patch 304 are attached to skin 306 of patient 300. Locating guide 302 is similar to any one of locating guides 102 and 202 described above or locating guide 600 shown in FIG. 9. Similarly, electrode patch 304 is similar to any one of electrode patches 104, 204 or 206 described above. Alternatively, locating guide 302 and electrode patch 304 may be attached to form a locating member, such as locating member 506 shown in FIG. 8.

Sacrum 308, a part of spinal canal 310, and Ilium bone 312 of patient 300 are shown in phantom. Sacrum includes S2, S3, and S4 foramen 314, 316, and 318, respectively, through which the S2, S3, and S4 sacral nerves, respectively, are accessible. The S1 foramen is not shown in FIG. 5. If a clinician wishes to implant a stimulation lead near the S3 sacral nerve, the clinician typically locates S3 foramen 316 because as previously stated, the S3 sacral nerve is accessible through S3 foramen 316. The clinician may use system 301 in accordance with the invention to locate S3 foramen 316.

In order to locate the S3 foramen, the clinician first positions and attaches locating guide 302 to skin 306 of patient 300. Preferably skin 306 is dry and unbroken. Patient 300 may be in any position that gives the clinician access to sacrum 308. However, the prone position is preferred in some embodiments because some types of electrical stimulation require testing of toe flexure, foot rotation, or a bellows response of the anus.

Preferably, locating guide 302 is positioned to frame the general area in which the S3 sacral foramen 314 is located. The clinician may use the boney landmarks of patient 300 to estimate the general location of the S3 foramen. In the present example, the boney landmarks are the crest of Ilium bone 312 and the lower part of spinal canal 310, which runs through sacrum 308. As FIG. 5 illustrates, first portion 302A of locating guide 302 overlays Ilium bone 312 of patient 300 and second portion 302B overlays a part of spinal canal 310.

After locating guide 302 is attached to skin 306 of patient 300, locating guide 302 frames an area within which the S3 sacral foramen 314 is located. This is referred to as area of interest 320, which is outlined with phantom lines in FIG. 5. Area of interest 320 represents the general area in which the S3 foramen is most likely located. Of course, there may be certain patients in which area of interest 320 is inaccurate, in which case, the clinician may need to readjust the position of locating guide 302.

After area of interest 320 is framed by locating guide 302, electrode patch 304 is attached to skin 306 of patient 300 within area of interest 320. Electrode patch 304 is electrically coupled to EIT instrument 305 by ribbon connector 322. After electrode patch 302 is in position, the clinician may begin imaging the tissue underlying electrode patch 302 using EIT instrument 305.

EIT instrument 305 causes current to flow between different pairs of electrodes in electrode patch 304. EIT instrument 305 uses the current flow patterns beneath the skin surface to formulate a two-dimensional impedance image that corresponds to the tissue structure underlying electrode patch 304. The resulting image conveys information relating to the presence and location of nerve sites. As previously discussed, based on the electrical characteristics of nerve tissue, a nerve is typically the area with the highest impedance. The resulting image may represent different impedance regions by, for example, color coding. In the present embodiment, sacral foramina 314, 316, and 318 are represented in the resulting image as areas of high impedance because the EIT instrument images the sacral nerves that are exposed through each foramen.

The clinician may determine a more precise location of the S3 foramen 314. The clinician can reference the image based on the resulting image generated by EIT instrument 305, which may be presented on the EIT instrument 305 display, as well as locating guide 302 and electrode patch 304 (in particular, aperture 307 and outer edges 304A, 304B, 304C, and 304D of electrode patch 304) to relate the image to actual locations within patient 300. As discussed above, a coordinate system may also be used to relate a region shown in the image to an actual location within patient 300. That is, the clinician may register the EIT image to an actual locating at patient 300 based using locating guide 302 and electrode patch 304 as reference points.

If S3 sacral foramen 314 is not clearly shown in the EIT image, the clinician may adjust a position of electrode patch 304, e.g., within area of interest 320 framed by locating guide 302, and generate another image using EIT instrument 305. The clinician may reference the initial image, as well as locating guide 302, in order to approximate the appropriate magnitude and direction of movement for electrode patch 304.

Once the S3 sacral foramen 314 is located, the image further helps the clinician accurately guide an introducer needle into the S3 foramen 314. As known in the art, once the introducer needle is introduced into the S3 foramen 314, an electrical stimulation lead may be inserted through the introducer needle, and implanted proximate to the S3 sacral nerve. The exact location of the S3 sacral nerve may be determined by testing patient's 300 responses to electrical stimulation that is delivered through the stimulation lead, e.g., from an external stimulator that is coupled to a proximal end of the lead.

Figure 6:
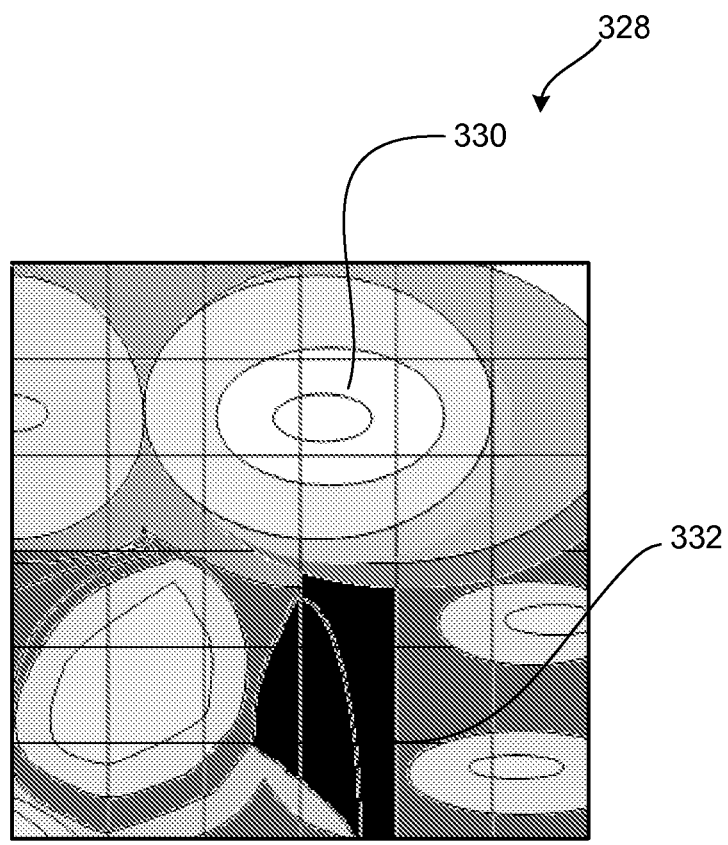
FIG. 6 illustrates an example of an image of the tissue composition underlying the electrode patch of FIG. 4, where the image is generated by an EIT instrument.

FIG. 6 illustrates an example of image 328 produced by EIT instrument 305. Image 328 corresponds to the tissue composition underlying electrode patch 304 in FIG. 5. In image 328, the shading represents the different impedance values of the subcutaneous tissue underlying electrode patch 304 in FIG. 5. Tissue exhibiting relatively low impedance values (e.g., nerve tissue) are shown as lighter regions (e.g., region 330) relative to higher impedance tissue (e.g., muscle), which are shown as dark regions (e.g., region 332). The clinician may interpret FIG. 6 as showing the presence of the S3 sacral foramen 314 in region 330. Region 330 can be related to an actual location on patient 300 by referencing locating guide 302 and outer edges 304A, 304B, 304C, and 304D of electrode patch array 304 with image 328. In this way, the clinician pinpoints the location of the S3 foramen 314 relative to aperture 307 in electrode patch 304. If desired, the clinician may remove electrode patch 304 from skin 306 and reattach electrode patch 304 in a different portion of area of interest 320. This may be desirable, for example, if it appears from image 328 that electrode patch 304 is not positioned close to the S3 foramen 314.

If the clinician introduces the introducer needle into aperture 307 in electrode patch 304, and the S3 foramen 314 is not found in the first attempt, the clinician may also use the image shown in FIG. 6 and locating guide 302 to readjust the path of the needle or readjust the position of electrode patch 304.

Locating S3 foramen 314 or another target nerve site with the aid of a system including a locating guide, electrode patch, and EIT instrument, such as to implant a medical member, may contribute to the efficiency of the medical member implantation process. For example, EIT instrument 305 requires a short run time to generate a useful image 328 of the target tissue site. In the embodiment discussed in reference to FIGS. 5-6, it is expected to take about one minute for EIT instrument 305 to image the tissue underlying electrode patch 304. As another example, the locating system described herein enables a clinician to implant the medical lead or another medical member as an out-patient procedure.

Figure 7:
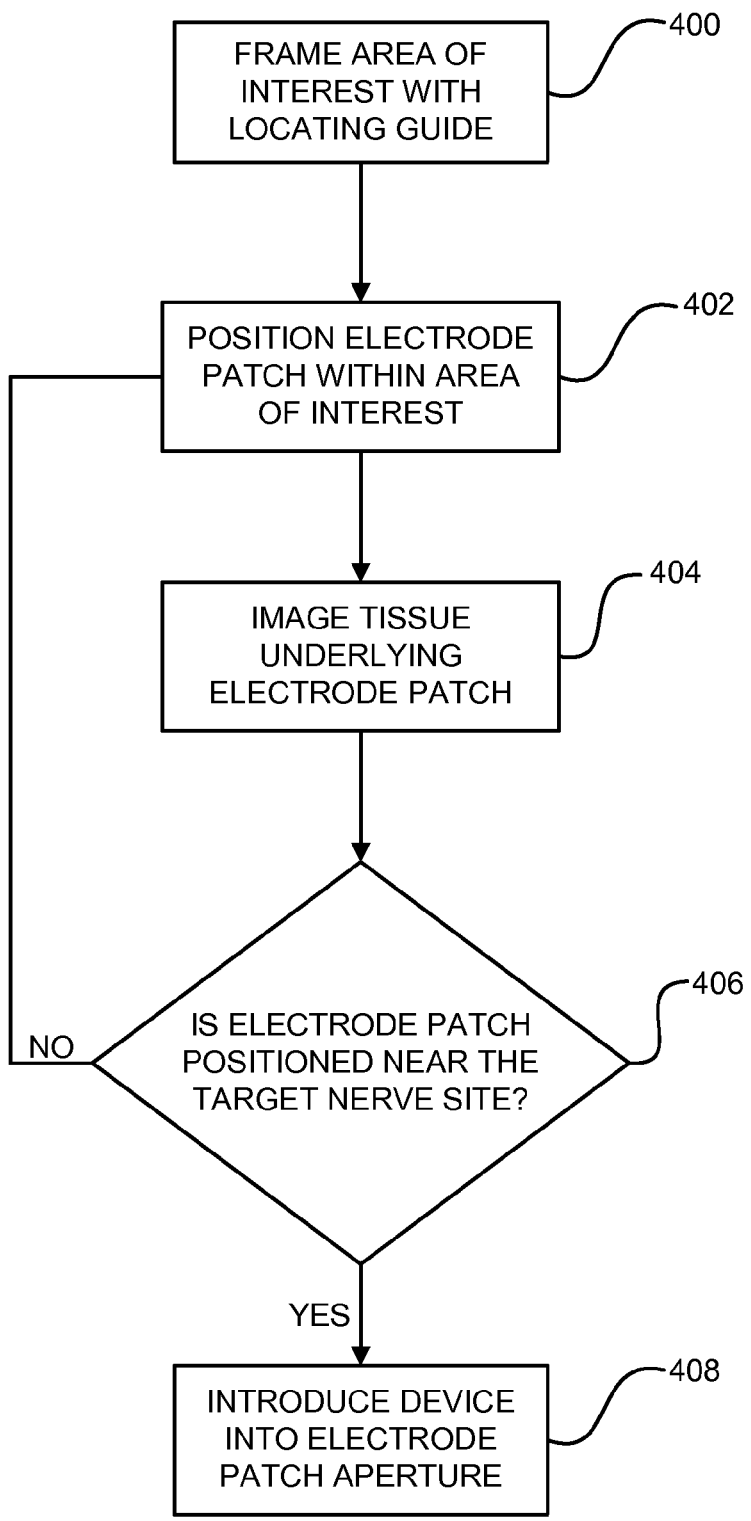
FIG. 7 is a flow diagram illustrating one embodiment of a method of locating a target nerve site and implanting a medical lead proximate to the target nerve site using an EIT-based imaging technique.

FIG. 7 is a flow diagram illustrating an exemplary method of locating a nerve site in order to implant a medical lead in accordance with the invention. As shown in FIG. 7, a locating guide is positioned on a patient to frame an area of interest in the vicinity of the medical lead implantation site (400). Next, an electrode patch is positioned within the framed area of interest (402). Thereafter, the tissue underlying the electrode patch is imaged, such as by using an EIT instrument (404). If an image is generated, a clinician may review the image to determine whether the electrode patch is positioned in a suitable position (i.e., over the desired implantation site) (406). For example, the clinician may determine whether the target nerve site is represented in the image. As another example, if the electrode patch includes an aperture, the clinician may determine whether the target nerve site is accessible through the aperture in the electrode patch. Alternatively, another EIT instrument may provide an output (e.g., a visual or audible indicium) indicating whether the electrode patch is positioned in a suitable position (406).

If the electrode patch is not positioned near the target nerve site, the clinician may reposition the electrode patch within the framed area of interest using the locating guide as a reference point (402) and re-image the tissue underlying the repositioned electrode patch (404). The process of repositioning the electrode patch relative to the locating guide is repeated until the electrode patch (and/or any aperture defined by the patch) is in a suitable position. Once the electrode patch is in a suitable position, the clinician may introduce a device (e.g., an introducer needle or another guide means for a medical lead) into an aperture in the electrode patch (408).

Figure 8:
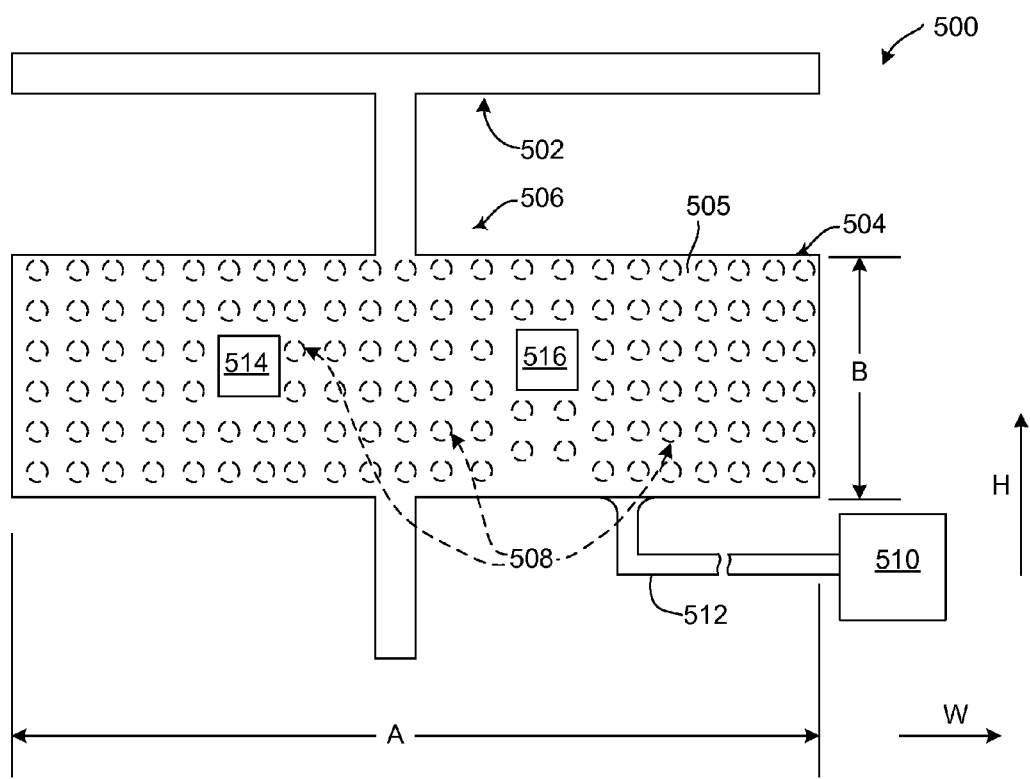
FIG. 8 is a plan view of a system for locating a target nerve site for implantation of a medical lead including a locating member within a locating guide attached to an electrode patch, in accordance with another embodiment of the invention.

FIG. 8 is a plan view of another embodiment of system 500 in accordance with the invention. In system 500, locating guide portion 502 and electrode patch 504 portion are mechanically coupled together to collectively form locating member 506. Locating guide portion 502 and electrode patch portion 504 may be integral, or may be two separate pieces attached by a suitable means, such as an adhesive. In one embodiment where locating member 506 is an integral piece, locating guide portion 502 and nonconductive backing 505 of electrode patch portion 504 are formed from a single piece of material (e.g., silicon or polyimides). For example, if locating member 506 is formed using circuit technology, locating guide portion 502 and nonconductive backing may be constructed from a single piece of polyimide film and electrode pads and conductive traces may be formed in the region identified to be electrode patch portion 506.

In order to locate a target nerve site, a clinician need only attach locating member 506 to skin of a patient, rather than a separate locating guide portion 502 and electrode patch portion 504. Locating guide portion 502 of locating member 506 is configured to be placed over boney landmarks of a patient (e.g, portion 502A is configured to overlay the spinal canal of a patient) and electrode patch portion 504 is placed with respect to locating guide portion 502 in the general vicinity of the target sacral foramen. Electrode patch portion 504 includes a plurality of electrodes 508 (shown in phantom), which are coupled to EIT apparatus 510 with ribbon connector 512.

In system 500, locating member 506 is tailored to locate specific sacral foramina because the placement of electrode patch portion 504 with respect to locating guide portion 502 is predetermined. The placement of electrode patch portion 504 with respect to locating guide portion 502 may be determined based on the average location of the target sacral foramen in humans with respect to the Ilium bone and spinal canal (i.e., the boney landmarks locating guide portion 502 is configured to overlay). In the embodiment shown in FIG. 8, locating member 506 is configured to locate foramen on both sides of a sacrum because electrode patch portion 504 includes two apertures 514 and 516 disposed on opposite sides of portion 502A of locating guide portion 502. In other embodiments, locating guide 506 may include a single aperture or more than two apertures. In yet other embodiments, one or more apertures may be disposed on a single side of portion 502A of locating guide portion.

Dimension A of electrode patch portion 504 extends across an entire width of locating member 506. In one embodiment, dimension A is about 12 cm to about 15 cm. In alternate embodiments, dimension A of electrode patch portion 504 may be greater than or less than a width (measured along direction W) of locating member 506. In one embodiment, dimension B of electrode patch portion 504 is about 3-6 cm. However, in other embodiments, dimension B may be any suitable length, and may, for example, extend across a height (measured along direction H) of locating member 506. Other dimensions of electrode patch portion 504 are also contemplated, and may depend upon the size of the patient, the target nerve site being located, and so forth.

Figure 9:
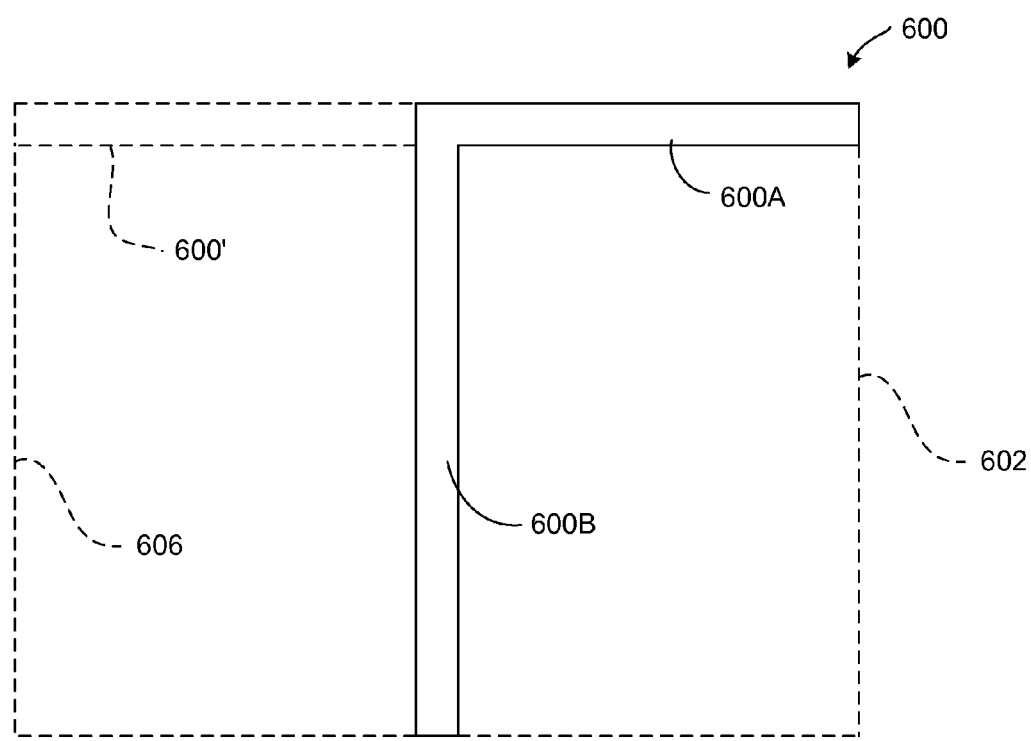
FIG. 9 is a plan view of another embodiment of a locating guide.

FIG. 9 is a plan view of another embodiment of locating guide 600, which includes first and second portions 600A and 600B, respectively. Locating guide 600 is similar to locating guides 100 and 200 in FIGS. 2 and 4, respectively, except that locating guide 600 is an L-shape. In a system for locating a sacral foramen, first portion 600A may overlay the posterior protuberance of the patient's Ilium bone and second portion 602B may overlay a part of the patient's spinal canal.

Unlike T-shaped locating guides 100 and 200, however, locating guide 600 frames area of interest 602 that is in the general vicinity of only one side of sacrum 24 (i.e., on one side of a midline of patient 18). If it is desirable to locate foramina on both sides of sacrum 24, where the two "sides" are divided by the spinal canal (i.e., on both sides of second portion 600B of locating guide 600), locating guide 600 may be flipped over, as shown by locating guide 600' (in phantom). In this way, locating guide 600 includes two skin-contact surfaces. Both skin contact surfaces of locating guide 600 may include an adhesive or other attachment mechanism.

Various embodiments of the invention have been described. Although implantation of leads has been described for purposes of illustration, the techniques described in this disclosure may be used to aid implantation of other devices, such as catheters, leadless stimulators, and other devices. These and other embodiments are within the scope of the following claims.

The invention claimed is:

1. A system comprising:
  a locating guide that frames an area of interest upon placement over skin of a patient;
  an electrode patch defining an aperture and including two or more electrodes, wherein the electrode patch is configured for placement within the area of interest while the locating guide is placed over skin of the patient and framing the area of interest; and
  a medical imaging device that indicates a location of a target tissue site within the patient based on electrical signals generated by one or more of the electrodes.

2. The system of claim 1, wherein the medical imaging device generates an image representing a tissue composition underlying the electrode patch, wherein the image indicates the location of the target tissue site.

3. The system of claim 2, wherein the medical imaging device includes an electrical impedance tomography instrument.

4. The system of claim 1, wherein the electrode patch has a substantially rectangular shape.

5. The system of claim 1, wherein the aperture has a width of at least approximately five millimeters wide and a length of at least approximately five millimeters.

6. The system of claim 1, wherein the locating guide is sized and shaped to substantially conform to a size and shape of at least a portion of a boney landmark of the patient.

7. The system of claim 6, wherein the boney landmark comprises an Ilium bone and spinal canal of a human patient.

8. The system of claim 1, wherein the locating guide comprises a plurality of distance marks.

9. The system of claim 1, wherein the target tissue site includes at least one of a S2 sacral foramen, a S3 sacral foramen or a S4 sacral foramen.

10. The system of claim 1, wherein the electrode patch is a first electrode patch defining a first aperture, the system further comprising a second electrode patch defining a second aperture and including two or more electrodes for placement within the area of interest.

11. The system of claim 10, wherein the medical imaging device indicates a first location of a first target tissue site within the patient based on electrical signals generated by one or more of the electrodes of the first electrode patch and a second location of a second target tissue site within the patient based on electrical signals generated by one or more of the electrodes of the second electrode patch.

12. The system of claim 1, wherein at least one of the electrodes of the electrode patch comprises a small gauge needle.

13. The system of claim 1, wherein the electrode patch defines a plurality of apertures.

14. The system of claim 1, wherein a nonconductive backing of the electrode patch and the locating guide are each composed at least in part of a flexible material.

15. The system of claim 1, further comprising an electrically conductive material disposed between each electrode and the skin of the patient.

16. The system of claim 15, wherein the electrically conductive material comprises at least one of a NaCl gel, tragacanth gum including a conductive additive, karaya gum including a conductive additive or acrylates including a conductive additive.

17. The system of claim 1, wherein the locating guide and electrode patch are connected.

18. The system of claim 1, wherein the locating guide and the electrode patch are configured such that a position of the electrode patch is adjustable relative to the locating guide while the locating guide is placed over skin of the patient.

19. The system of claim 1, further comprising:
an electrical stimulator; and
an implantable medical lead, coupled to the electrical stimulator, configured to deliver stimulation to the target tissue site.

20. The system of claim 1, further comprising:
a fluid delivery device; and
a catheter configured to delivers a fluid from the fluid delivery device to the target tissue site.

21. A method comprising:
positioning a locating guide over skin of a patient to frame an area of interest;
positioning an electrode patch within the area of interest while the locating guide is over skin of the patient and framing the area of interest, wherein the electrode patch is movable relative to the locating guide, and wherein the electrode patch includes at least two electrodes; and
locating a target tissue site within the patient based on electrical signals generated by one or more of the electrodes.

22. The method of claim 21, wherein locating the target tissue site comprises generating an image indicating the location of the target tissue site based on the electrical signals.

23. The method of claim 21, further comprising:
generating an image of tissue of the patient underlying the electrode patch with a medical imaging device;
repositioning the electrode patch within the area of interest based on the image.

24. The method of claim 21, wherein locating the target tissue site comprises applying electrical impedance tomography to the electrical signals to indicate the location of the target tissue site.

25. The method of claim 21, wherein positioning a locating guide over a skin of a patient to frame an area of interest comprises positioning the locating guide over a boney landmark of the patient.

26. The method of claim 21, wherein the area of interest is a sacrum of a human patient, and wherein the target tissue site is one of a S2 foramen, a S3 foramen, and a S4 sacral foramen.

27. The method of claim 21, wherein the electrode patch defines an aperture, the method further comprising:
introducing an introducer needle into the aperture;
introducing a medical member into the introducer needle; and
positioning the medical member proximate to the target tissue site.

28. The method of claim 27, further comprising adjusting a path of the introducer needle within the aperture.

29. A system for locating a sacral foramen of a patient, the system comprising:
a locating guide for placing on skin of the patient, wherein the locating guide frames a region of skin proximate to a sacrum of the patient;
an electrode patch defining an aperture and including two or more electrodes configured for placement within the region of skin proximate to the sacrum while the locating guide is on skin of the patient and framing the region of skin; and
a medical imaging device that indicates a location of the sacral foramen based on electrical signals generated by one or more of the electrodes.

30. The system of claim 29, wherein the locating guide is configured to be placed over at least a part of at least one of an Ilium bone or a spinal canal of the patient.

31. The system of claim 29, wherein the medical imaging device includes an electrical impedance tomography instrument.

32. A method for locating a sacral foramen of a patient, the method comprising:
positioning a locating guide over at least a part of at least one of an Ilium bone or a spinal canal of the patient to frame a region of skin overlaying at least a part of a sacrum of the patient;
positioning an electrode patch defining an aperture and including two or more electrodes for placement within the region of skin overlaying the sacrum while the locating guide is positioned to frame the region of skin overlaying at least the part of the sacrum of the patient; and
locating the sacral foramen based on electrical signals generated by one or more of the electrodes.

33. The method of claim 32, further comprising introducing a medical element into the patient through the aperture of the electrode patch.

34. The system of claim 1, wherein the locating guide is configured to be placed over skin of the patient and frame the area of interest while the electrode patch is placed over the skin of the patient within the area of interest.

35. The system of claim 1, wherein the area of interest is uncovered by the locating guide.

* * * * *

UNITED STATES PATENT AND TRADEMARK OFFICE
CERTIFICATE OF CORRECTION

PATENT NO. : 9,439,581 B2
APPLICATION NO. : 11/835290
DATED : September 13, 2016
INVENTOR(S) : Dinsmoor et al.

It is certified that error appears in the above-identified patent and that said Letters Patent is hereby corrected as shown below:

In the Claims

Column 19, Line 35: "catheter configured to delivers" should read --catheter configured to deliver--

Signed and Sealed this
Thirteenth Day of March, 2018

Andrei Iancu
*Director of the United States Patent and Trademark Office*